(12) United States Patent
Kimura et al.

(10) Patent No.: US 8,703,739 B2
(45) Date of Patent: Apr. 22, 2014

(54) INTRAVASCULAR INDWELLING CATHETER LOCK SOLUTION CONTAINING WEAK ACID AND CONTAINER CONTAINING THE SAME

(75) Inventors: Yuko Kimura, Hiroshima (JP); Koji Suzuki, Hiroshima (JP); Minoru Iwata, Hiroshima (JP); Sumika Iwamoto, Hiroshima (JP); Takashi Yamamoto, Hiroshima (JP)

(73) Assignee: JMS Co., Ltd., Hiroshima-shi (JP)

( * ) Notice: Subject to any disclaimer, the term of this patent is extended or adjusted under 35 U.S.C. 154(b) by 119 days.

(21) Appl. No.: 13/133,123

(22) PCT Filed: Dec. 5, 2008

(86) PCT No.: PCT/JP2008/072186
§ 371 (c)(1),
(2), (4) Date: Sep. 14, 2011

(87) PCT Pub. No.: WO2010/064324
PCT Pub. Date: Jun. 10, 2010

(65) Prior Publication Data
US 2011/0315583 A1    Dec. 29, 2011

(51) Int. Cl.
*A61K 31/727* (2006.01)

(52) U.S. Cl.
USPC .......................................................... 514/56

(58) Field of Classification Search
None
See application file for complete search history.

(56) References Cited

U.S. PATENT DOCUMENTS

| | | |
|---|---|---|
| 2004/0092890 A1 | 5/2004 | Ash |
| 2005/0215978 A1 | 9/2005 | Peter et al. |
| 2006/0177477 A1 | 8/2006 | Ash et al. |

FOREIGN PATENT DOCUMENTS

| | | | |
|---|---|---|---|
| JP | 2002-052336 A | 2/2002 | |
| JP | 2003-183154 A | 7/2003 | |
| JP | 2005-517460 A | 6/2005 | |
| JP | 2006-232829 A | 9/2006 | |
| JP | 2008-100926 A | 5/2008 | |
| WO | WO 2005123149 A1 | * | 12/2005 |

OTHER PUBLICATIONS

JP 2002-052336, Feb. 2002, machine translation.*
Hep-Lock, Drugs.com, Jan. 2007.*
International Search Report for PCT/JP2008/072186, mailing date of Jan. 13, 2009.
J. L. Gerberding et al., "Guidelines for the Prevention of Intravascular Catheter-Related Infections", Morbidity and Mortality Weekly Report, Recommendations and Reports, Centers for Disease Control and Prevention, (Aug. 9, 2002), vol. 51, No. RR-10, pp. 1-34.
"Thoroughgoing Preventative Measure against Nosocomial Infection with Serratia", Ministry of Health, Labor and Welfare, Pharmaceutical and Food Safety Bureau, Safety Division Information, Pharmaceutical and Medical Safety No. 0719001, (Jul. 19, 2002), pp. 1-2.
Drug Intelligence and Clinical Pharmacy, vol. 9, pp. 154-155, (1975).
K. J. Henrickson et al., "Prevention of Central Venous Catheter-Related Infections and Thrombotic Events in Immunocompromised Children by the Use of Vancomycin/Ciprofloxacin/Heparin Flush Solution: A Randomized, Multicenter, Double-Blind Trial", Journal of Clinical Onocology, vol. 18, No. 6, (Mar. 2000), pp. 1269-1278.
J. Carratala et al., "Randomized, Couble-Blind Trial of an Antibiotic-Lock Technique for Prevention of Gram-Positive central Venous Catheter-Related Infection in Neutropenic Patients with Cancer", Antimicrobial Agents and Chemotherapy, (Sep. 1999), vol. 43, No. 9, pp. 2200-2204.
C. Schwartz et al., "Prevention of Bacteremia Attributed to Luminal Colonization of Tunneled Central Venous Catheters With Vancomycin-Susceptible Organisms", Journal of Clinical Onocology, vol. 8, No. 9, (Sep. 1990), pp. 1591-1597.
I. Raad et al., "Minocycline and Ethylenediaminetetraacetate for the Prevention of Recurrent Vascular Catheter Infections", Clinical Infections Diseases, The University of Chicago, (1997), vol. 25, pp. 149-151.

* cited by examiner

*Primary Examiner* — Layla Bland
(74) *Attorney, Agent, or Firm* — Westerman, Hattori, Daniels & Adrian, LLP

(57) ABSTRACT

A catheter lock solution which is a catheter lock preparation having a bacteriostatic property at physiological osmotic pressure without practically containing a bacteriostatic component such as a preservative, an antimicrobial agent, or an antibiotic and having high safety, characterized in that the preparation contains a weak acid having an acid dissociation constant (pKa) of 3.0 to 6.5 as a buffer, a pH of the solution is less than 6.0, preferably from 3.0 to about 5.5, an osmotic pressure ratio is from 0.5 to 3.0, and a pH change (variation) can be suppressed to less than the 6.0 with the weak acid, and a container containing the catheter lock solution.

3 Claims, No Drawings

INTRAVASCULAR INDWELLING CATHETER LOCK SOLUTION CONTAINING WEAK ACID AND CONTAINER CONTAINING THE SAME

TECHNICAL FIELD

The present invention relates to a catheter lock solution which is a solution having a bacteriostatic effect and being injected into a lumen of a catheter indwelled in a blood vessel of a patient, and also relates to a container containing the lock solution.

BACKGROUND ART

Nosocomial infection is an important problem to be solved by modern medicine because it threatens patient lives and also, for hospitals, it extends the periods of hospitalization and causes excessive medical expenses. Main routs of nosocomial infection include (1) medicine contamination during preparation of medicines, and (2) contamination of routes of medicine administration. As a preventive measure against the contamination, (1) a preparation pre-filled in a syringe is used for decreasing the opportunity of medicine contamination, and (2) a medical apparatus with a closed flow path is developed for decreasing the contamination of routes of administration.

An intravascular indwelling catheter is a tube inserted into a blood vessel in order to administer an infusion preparation or medicine into blood. In medical practice, a peripheral venous catheter and a central venous catheter are frequently used for access to blood vessels, and these catheters are typical examples of the intravascular indwelling catheter. The intravascular indwelling catheter is considered as a source of nosocomial infection and seen as a problem. For example, an intravascular catheter induces local infection, bloodstream infection, or septicemia. As countermeasures against this, various approaches such as the establishment of guidelines (Non-patent Document 1 below) have been made. As one of the approaches, in the case of a patient who is treated with an infusion through the intravascular indwelling catheter over a long period of time, catheter lock is performed for preventing occlusion of the catheter in a routine operation in which for the reason of bathing or bedding, an infusion line is removed from the patient, leaving the intravascular indwelling catheter indwelled.

The catheter lock includes filling a catheter with physiological saline or heparin diluted with physiological saline as a catheter lock solution, and enclosing the solution generally for about 24 hours. As the catheter lock solution, heparin-saline having an anticoagulant action is often used, but in some cases, a physiological saline is used for locking a peripheral venous catheter for a short time. Intravascular indwelling of a catheter locked with the catheter lock solution is widely conduced because it is advantageous in that the frequency of needling to a patient is decreased, and the time required for a medical staff to insert a catheter is reduced. However, when a catheter is contaminated with bacteria during catheter lock, the bacteria proliferate in the catheter warmed by the body temperature, and sometimes a biofilm is formed to cause the risk of infection. For example, in 2002 in Japan, a heparin-saline solution prepared in advance was contaminated with bacteria, and patients administered with the heparin-saline solution as a catheter lock solution developed septicemia one after another, leading to death of several patients. With this accident as a turning point, the risk of infection with catheter lock solutions is recognized (Non-patent Document 2 below), and in principle, catheter lock solutions composed of heparin are prohibited from being prepared in advance in hospitals.

Disclosed is a syringe filled with a solution which is characterized by containing 1 to 100 units/mL of heparin, being physiologically isotonic, and having a pH 6 or more, without containing a preservative (Patent Document 1). This catheter lock solution is an aseptic preparation pre-filled in a syringe and is sold, and thus the opportunity of contamination during preparation in a hospital is decreased, thereby possibly decreasing nosocomial infection. However, the catheter lock solution, i.e., physiological saline or heparin-saline, does not have an antimicrobial/bacteriostatic action and thus bacteria proliferate when contaminated with bacteria as shown by data later, and thus it cannot be easily said that nosocomial infection is eradicated. That is, even when a patient is administered with an aseptic catheter solution pre-filled in a separate container connected to an administration line such as an infusion set, there is the risk of contamination of the catheter with bacteria due to the use of the contaminated infusion set or improper treatment and operation by a practitioner. As a result, bacteria proliferate in the catheter lock solution, and a large amount of bacteria enter the blood stream, thereby causing serous infections. In particular, in the case of an intravascular indwelling catheter, the catheter lock solution comes in contact with blood in the catheter and thus creates an environment more suitable for bacterial proliferation due to blood-derived nutrient sources.

A heparin preparation with the antimicrobial action, which contains, as a preservative, methyl paraoxybenzoate, propyl paraoxybenzoate, chlorobutanol, cresol, phenol, or benzyl alcohol, is sold. However, it is reported that administration of a large amount of benzyl alcohol brings about dyspnea or allergy reaction (Non-Patent Document 3 below), and the above-described toxic preservative agent is no longer used from the viewpoint of safety. In addition, in order to prevent catheter-related bloodstream infection, an antibiotic lock method has been attempted, in which a lumen of a catheter is flushed and filled with a solution of vancomycin which is an antibiotic, and the effect has been proved (Non-Patent Documents 4, 5, and 6). However, according to the guidelines of Non-Patent Document 1, this method is not recommended from the viewpoint of the risk of producing resistant bacteria.

Also, an anticoagulant agent/antimicrobial agent combination containing minocycline as an antibiotic and ethylenediaminetetraacetic acid has been proposed as a catheter lock solution and investigated (Non-Patent Document 7 below). Further, a concentrated citrate solution is disclosed as a catheter lock solution for decreasing infections (Patent Document 2 below), but bacteremia is improved by the antimicrobial action of a 47% hypertonic citrate solution (supposed to be about 6000 mOs) as shown in Examples. Such a high-concentration citrate lock solution remote from physiological osmotic pressure have the concern about safety because it takes in blood calcium and forms a complex, thereby possibly causing the occurrence of hypocalcemia or the like.

Patent Document 1: Japanese Unexamined Patent Application Publication No. 2003-183154

Patent Document 2: Japanese Unexamined Patent Application Publication (Translation of PCT Application) No. 2002-523336

Non-Patent Document 1: Guidelines for the Prevention of Intravascular Catheter-Related infections (CDC) (Untied States, Morbidity and Mortality Weekly Report, Aug. 9, 2002)

Non-Patent Document 2: "Thoroughgoing Preventive Measure against Nosocomial Infection with Serratia", Ministry of Health, Labor and Welfare, Pharmaceutical and Food Safety Bureau, Safety Division Information (Pharmaceutical and Medical Safety No. 0719001, Jul. 19, 2002)

Non-Patent Document 3: Drug Intell Clin Pharm, 9, p 154, 1975

Non-Patent Document 4: Henrickson K J, Axtell R A, Hoover S M, et al.
Prevention of central venous catheter-related infections and thrombotic events in immunocompromised children by the use of vancomycin/ciprofloxacin/heparin flush solution: A randomized, multicenter, double-blind trial (J Clin Oncol 2000; 18: 1269-78)

Non-Patent Document 5: Carratala J, Niubo J, Fernandez-Sevilla A, et al.
Randomized, doubleblind trial of an antibiotic-lock technique for prevention of grampositive central venous catheter-related infection in neutropenic patients with cancer (Antimicrob Agents Chemother 1999; 43: 2200-4)

Non-Patent Document 6: Schwartz C, Henrickson K J, Roghmann K, Powell K,
PREVENTION OF BACTEREMIA ATTRIBUTED TO LUMINAL COLONIZATION OF TUNNELED CENTRAL VENOUS CATHETERS WITH VANCOMYCIN-SUSCEPTIBLE ORGANISMS (J CLIN ONCOL 1990; 8: 1591-7)

Non-Patent Document 7: Raad I I, Buzaid A, Rhyne J, et al. Minocycline and ethylenediaminetetraacetate for the prevention of recurrent vascular catheter infections (Clin Infect Dis 1997; 25: 149-51)

DISCLOSURE OF INVENTION

Problems to be Solved by the Invention

A problem to be solved by the invention is to provide a catheter lock solution having high safety and a bacteriostatic property at physiological osmotic pressure without substantially containing a bacteriostatic component such as a preservative, an antimicrobial agent, or an antibiotic. In the present invention, the term "bacteriostatic action (effect)" represents that logarithmic proliferation of bacteria is suppressed, and bacterial proliferation within 24 hours can be generally suppressed to 100 times or less or about 100 times in terms of the number of bacteria, and includes both the effect of suppressing bacterial proliferation and the antimicrobial effect.

Means for Solving the Problems

The bacterial proliferation strongly depends on surrounding environments. That is, the proliferation rate and survival ratio of bacteria greatly vary with the types and concentrations of organic substances and salts serving nutrient sources, pH, and temperatures. Among these, the inventors studied with attention to pH. Namely, existing catheter lock solutions have pH ranging from weakly acidic pH to neutral pH but have a weak buffering ability and thus create environments (neutral pH region, blood-derived nutrient sources) suitable for bacterial growth particularly when coming in contact with blood. Therefore, the inventors studied relation between the pH of a catheter lock solution and bacterial proliferation. As described above, mixing of a catheter lock solution with a preservative and an antibiotic has been investigated so far, but studies about pH have not yet carried out. As a result of close research conducted by the inventors, first, it was found that even in an environment where a blood-derived nutrient source is present, when weak acidity of less than pH 6.0 is maintained, proliferation of bacteria mixed in a catheter lock solution is suppressed. Next, as a result of confirmation of the pH of existing catheter lock solutions and proliferation of bacteria, it was found that the pH of a heparin lock solution and the pH of physiological saline are 5.5 to 8.0 and 4.5 to 8.0, respectively, and are thus weakly acidic pH to neutral pH (the Japanese Pharmacopoeia, 15th edition), but these catheter lock solutions have the very weak pH buffering ability and thus do not exhibit the bacteriostatic action during locking of vascular indwelling catheters. That is, when a catheter is locked, the catheter lock solution is in contact with blood in the catheter, but the pH of the catheter lock solution is rapidly neutralized by mixing with blood because of the strong buffering ability of blood. Therefore, in order to solve the problem, research for the buffering ability of a catheter lock solution has been advanced, resulting in the development of a catheter lock solution capable of exhibiting the bacteriostatic action while maintaining pH of less than 6.0 even in contact with blood during catheter lock. This led to the completion of the present invention.

That is, the present invention provides an aqueous solution as a catheter lock solution inserted into an intravascular indwelling catheter and having a bacteriostatic action, the aqueous solution having a pH of less than 6.0 and an osmotic pressure ratio of 0.5 to 3.0 and containing an inorganic or organic acid as a buffer having an acid dissociation constant (pKa) of 3.0 to 6.5 at a concentration of 10 mM or more, and thus the above problem can be solved even by a catheter lock solution without substantially containing an antimicrobial substance such as a preservative, an antimicrobial agent, or an antibiotic. The expression "without substantially containing an antimicrobial substance such as a preservative, an antimicrobial agent, or an antibiotic" represents that the antimicrobial substance is not purposely added. For example, a conceivable case where a substance having an antimicrobial ability is eluted from a plastic container material using the substance having antimicrobial ability satisfies the requirement "without substantially containing" of the present invention.

The lower the pH of the catheter lock solution of the present invention, the more the bacteriostatic and antimicrobial effect on various types of bacteria can be exhibited. However, when pH is excessively low, the blood in contact with the catheter lock solution is changed in nature, and also the anticoagulant activity of heparin is decreased. Conversely, when the pH of the catheter lock solution is excessively high, the bacteriostatic and antimicrobial effect cannot be exhibited. Therefore, the acidic pH of the catheter lock solution of the present invention is generally 2.0 or more and less than 6.0, preferably about 3.0 to 5.5, depending on the buffering ability of a buffer added. However, as described above, when heparin inactivation is increased by adjusting the catheter lock solution of the present invention to low pH, for example, 2.0 or less, at which the bacteriostatic and bactericidal effect is sufficiently exhibited, both the bacteriostatic and bactericidal effect and the anticoagulant activity of the catheter lock solution can be satisfied by previously adding an excess of heparin in consideration of inactivation of the heparin. Therefore, the catheter lock solution of the present invention can be used even at pH 2.0 or less.

As the buffer, an inorganic acid or organic acid having an acid dissociation constant (pKa) of 3.0 to 6.5 in the weakly acidic region is preferred. With a compound having pKa within this range, even when blood is mixed, an increase in pH can be suppressed, and the pH can be maintained at 3.0 to 6.0. In particular, even for the catheter lock solution preferably having a pH near 5 to 6, it is preferred to use a buffer having such a high ability to suppress an increase in pH that the pH of the catheter lock solution can be maintained in the range of less than 6.0 after contact with blood. Examples of such a buffer include those used in Examples, such as a phosphate buffer, a citrate buffer, an acetate buffer, a succinate buffer, and a 3,3-dimethyl glutarate buffer. However, the buffer which can exhibits the advantages of the present invention is not limited to the phosphate buffer, citrate buffer, acetate buffer, succinate buffer, and 3,3-dimethyl glutarate buffer as long as it is a weak acid having a pKa of 3.0 to 6.5 which is physiologically allowable. The buffer containing, as the weak acid, for example, lactic acid (pKa: 3.64), malic acid (pKa: 3.23, 4.77), tartaric acid (pKa: 2.87, 3.97), ascorbic acid (pKa: 4.16, 11.73), glutamic acid (pKa: 2.19, 4.25, 9.67), or histidine (pKa: 5.85, 7.78), can be used.

In addition, the inorganic acid or organic acid preferably does not inhibit the efficacy of heparin. These weak acids can be used alone or in combination of two or more, and the pH range exhibiting the buffering ability can be extended by combining two or more weak acids. The buffer is required to have such a concentration that pH is maintained even by contact with blood, and the concentration is 10 to 250 mM, preferably about 50 to 150 mM. Further, in preparing the catheter lock solution, the osmotic pressure is preferably adjusted to be the same as the biological osmotic pressure using an osmoregulatory agent, for example, sodium chloride.

The type of a heparin solution is not particularly limited and, for example, a heparin solution generally used for preventing blood coagulation during use of an artificial heart-lung or another extracorporeal circulation device, preventing blood coagulation during insertion of a vascular catheter, or preventing blood coagulation during a blood transfusion or blood test can be used.

In addition, the catheter lock solution preferably has such viscosity that even when blood is mixed in the catheter lock solution in contact with the blood, diffusion of the blood in the catheter lock solution can be minimized. Therefore, a viscosity modifier is preferably used. Examples of such a viscosity modifier of the catheter lock solution include sodium carboxymethyl cellulose, polyvinylpyrrolidone, polyethylene glycol distearate, lauryldimethylamine oxide, fatty acid alkanol amide, methyl cellulose, Hypromellose, dextrin, hydroxymethyl(ethyl) cellulose, polyethylene glycol, glycerin, polyvinyl alcohol, sodium alginate, and the like.

The catheter lock solution of the present invention can be prepared by, for example, a method for producing a catheter lock solution, the method including the steps of preparing a catheter lock solution, for example, a physiological saline solution, containing 10 to 250 mM of an inorganic or organic acid having an acid dissociation constant (pKa) of 3.0 to 6.5 and an osmoregulatory agent in an amount effective to regulate the osmotic pressure ratio of the solution to 0.5 to 3.0, adjusting the pH of the solution to less than 6.0, and then filling a container with the solution and sealing the container. In addition, the osmotic pressure ratio of the catheter lock solution of the present invention is adjusted to 0.5 to 3.0 so that damage to the blood cells by the lock solution can be prevented, and irritation can be decreased.

When the catheter lock solution is the heparin solution, the catheter lock solution can be prepared by a method for producing a heparin catheter lock solution, the method including the steps of preparing a solution containing 1 to 1000 units/mL of heparin or a salt thereof, adjusting the pH of the solution to less than 6.0, and then filling a container with the solution and sealing the container. The heparin catheter lock solution produced by the preparation method is preferably heat-sterilized in the state of being filled in the container. As the heat sterilization temperature, a temperature range which is generally used as the heat sterilization temperature for catheter lock solutions, for example, about 105° C. to 120° C., can be used. In addition, it is preferred that the pH of the catheter lock solution after the heat sterilization can be maintained at less than 6.0.

A container which can be used as the container containing the heparin catheter lock solution, for example, has a structure in which at least two liquid-tight independent rooms are formed to be partitioned by a partition wall, and the partition wall is breakable so that a liquid is allowed to pass through the rooms by breaking the partition wall. In addition, one of the rooms contains neutral heparin sodium, and the other one room contains as the buffer an acidic aqueous solution of an inorganic acid or organic acid of pH with which an acidic aqueous heparin solution exhibiting the bacteriostatic effect while maintaining the anticoagulant activity of the heparin sodium can be prepared by mixing with the neutral heparin sodium. In addition, in the container, the components contained in the respective rooms can be mixed by breaking the partition wall, which partitions the rooms, before or after the heat-sterilization. Examples of the acidic aqueous solution of pH with which an acidic aqueous heparin solution exhibiting the bacteriostatic effect while maintaining the anticoagulant activity of the heparin sodium can be prepared by mixing with the neutral heparin sodium include the above-described inorganic acids and organic acids and buffers.

Advantages

According to the present invention, it is possible to provide a catheter lock preparation which has high safety and a bacteriostatic property at physiological osmotic pressure without practically containing a bacteriostatic component such as a preservative, an antimicrobial agent, or an antibiotic.

BEST MODE FOR CARRYING OUT THE INVENTION

Example 1

The pH and pH buffering ability of a catheter lock solution and bacterial proliferation were examined.

A 10 units/mL heparin catheter lock solution containing a 100 mM sodium phosphate buffer and having an osmotic pressure ratio adjusted to 1.0 with sodium chloride was prepared. The pH of this solution was adjusted with the sodium phosphate buffer to form five solutions of pH 6.0, 5.0, 4.0, 3.0, and 2.0. As known catheter lock solutions, a 0.9% sodium chloride solution (physiological saline) of pH 5.3 before addition of blood, two types of 10 units/mL heparin lock solutions, i.e., a heparin lock solution (commercial product A) of pH 6.7 and a heparin lock solution (commercial product B) of pH 6.0, were prepared (comparative examples). The osmotic pressure ratios of these solutions were all 1.0.

Assuming the case where a catheter lock solution comes in contact with blood in a catheter, 2% by volume of human blood was added to each of the catheter solutions of the example and the comparative examples, and pH was measured to measure the pH buffering ability of the catheter lock solution. Further, Staphylococcus aureus (strain No. IFO 13276) was inoculated into each of the catheter lock solutions to which human blood was added, followed by standing culture at 37° C. for 24 hours. The results are shown in Table 1. The pH values of the catheter lock solutions of the comparative examples were 5.3, 6.7, and 6.0, but all the pH values were increased to over 7 by adding 2% by volume of blood, creating an environment suitable for bacterial proliferation. Therefore, Staphylococcus aureus was proliferated 700 times or more for 24 hours. In contrast, the catheter lock solutions containing the buffer of the example showed small changes in pH after the addition of blood, and proliferation of Staphylococcus aureus was not observed. These results reveal that the known catheter lock solutions are neutralized by contact with blood to cause bacterial proliferation, and that when a pH of less than 6.0 is maintained by adding a proper buffer to a catheter lock solution, the bacteriostatic action is exhibited.

TABLE 1

| | | pH and buffering ability | | Results of culture of *Staphylococcus aureus* (CFU/mL) | |
|---|---|---|---|---|---|
| | | pH before addition of blood | pH after addition of 2% blood | Number of bacteria inoculated | Number of viable bacteria 24 hours after |
| Example | Lock solution containing 10 units/mL heparin and 100 mM Na phosphate | 6.0 | 6.0 | 61 | 47 |
| | | 5.0 | 5.3 | 61 | 3 |
| | | 4.0 | 4.8 | 61 | 0 |
| | | 3.0 | 3.3 | 61 | 0 |
| | | 2.0 | 2.1 | 61 | 0 |
| Comparative Example | Physiological saline | 5.3 | 7.3 | 60 | 42000 |
| | Heparin lock solution (commercial product A) | 6.7 | 7.3 | 60 | 73000 |
| | Heparin lock solution (commercial product B) | 6.0 | 7.3 | 60 | 220000 |

Example 2

Catheter lock solutions containing 50, 100, and 150 mM of buffer and having an osmotic pressure regulated with sodium chloride and a pH of 3 to 5 were prepared (Example). For comparison, a physiological saline solution of pH 3 to pH 5 was prepared as a catheter lock solution not containing a buffer (Comparative Example 1). Further, a glycine-buffer was prepared as an example of a buffer which was difficult to maintain in the pH range of 3 to 6 (Comparative Example 2). The pHs of all test solutions were adjusted with hydrochloric acid or sodium hydroxide. The buffering ability of each of the catheter lock solutions of Example and Comparative Examples was tested. Assuming the case where the catheter lock solution came in contact with blood in a catheter, changes in pH by adding 2% of blood were examined.

As a result, the pH values of physiological saline solutions adjusted to pH 3.0, 4.0, and 4.9 were greatly increased to 4.9, 7.0, and 7.2, respectively, by adding 2% blood and were not maintained in the target pH range of 3 to 6. In addition, in the comparative example in which glycine was added as a buffer, the pH was increased to 6.53 by adding 2% by volume of blood to the catheter lock solution adjusted to pH 5.01 at a glycine concentration of 100 mM. This result indicates that glycine (pKa: 2.91, 6.81, 8.33) has the weak buffering ability near pH 5 and is incompatible with the buffer of the present invention. On the other hand, the lock solution containing a buffer composed of a weak acid having pKa in the range of 3.0 to 6.5 showed a slight change in pH even by adding 2% of blood as compared with the comparative example. In particular, a pH of less than 6.0 was maintained even by adding 2% by volume of blood to the catheter lock solution adjusted to near pH 5 (Tables 2 and 3). These results indicate that a weak acid having pKa in the range of 3.0 to 6.5 can maintain weakly acidic pH required for exhibiting the bacteriostatic action in a concentration range showing physiological osmotic pressure.

TABLE 2

| Buffer | Buffer pKa | Buffer concentration | Osmotic pressure (mOsm) | pH Before addition of blood | pH After addition of 2% blood |
|---|---|---|---|---|---|
| <Comparative Example 1> No | — | — | 288 | 3.04 | 4.90 |
| | | | 288 | 4.04 | 7.01 |
| | | | 288 | 4.91 | 7.23 |

TABLE 2-continued

| Buffer | Buffer pKa | Buffer concentration | Osmotic pressure (mOsm) | pH Before addition of blood | pH After addition of 2% blood |
|---|---|---|---|---|---|
| <Comparative Example 2> | 2.91 | 50 mM | 287 | 2.96 | 3.19 |
| | | | 285 | 3.97 | 4.82 |
| | | | 286 | 4.99 | 6.85 |
| Glycine-buffer | 6.81 | 100 mM | 287 | 2.95 | 3.11 |
| | 8.33 | | 285 | 3.97 | 4.41 |
| | | | 286 | 5.01 | 6.53 |
| | | 150 mM | 293 | 2.94 | 3.07 |
| | | | 291 | 3.99 | 4.22 |
| | | | 291 | 4.99 | 5.79 |
| Phosphate-buffer | 1.83 | 50 mM | 290 | 2.89 | 3.18 |
| | 6.43 | | 280 | 3.90 | 4.75 |
| | 11.46 | | 291 | 4.80 | 5.17 |
| | | 100 mM | 285 | 2.87 | 3.06 |
| | | | 285 | 3.89 | 4.52 |
| | | | 284 | 4.86 | 5.07 |
| | | 250 mM | 292 | 2.89 | 3.06 |
| | | | 290 | 3.91 | 4.36 |
| | | | 290 | 4.90 | 5.06 |
| Citrate-buffer | 2.90 | 50 mM | 288 | 2.84 | 3.00 |
| | 4.36 | | 286 | 3.82 | 3.94 |
| | 5.69 | | 289 | 4.82 | 4.91 |
| | | 100 mM | 281 | 2.89 | 3.03 |
| | | | 281 | 3.90 | 4.00 |
| | | | 282 | 4.91 | 4.98 |

TABLE 3

| Buffer | Buffer pKa | Buffer concentration | Osmotic pressure (mOsm) | pH Before addition of blood | pH After addition of 2% blood |
|---|---|---|---|---|---|
| Acetate-buffer | 4.76 | 50 mM | 289 | 2.91 | 3.70 |
| | | | 292 | 3.85 | 4.17 |
| | | | 289 | 4.89 | 5.08 |
| | | 100 mM | 285 | 2.89 | 3.51 |
| | | | 283 | 3.85 | 4.13 |
| | | | 286 | 4.91 | 5.08 |
| | | 150 mM | 286 | 2.88 | 3.51 |
| | | | 289 | 3.88 | 4.14 |
| | | | 287 | 4.95 | 5.10 |
| Phthalate-buffer | 2.75 | 50 mM | 278 | 2.85 | 3.20 |
| | 4.90 | | 295 | 3.82 | 4.20 |
| | | | 279 | 4.86 | 5.05 |

TABLE 3-continued

| Buffer | Buffer pKa | Buffer concentration | Osmotic pressure (mOsm) | pH Before addition of blood | pH After addition of 2% blood |
|---|---|---|---|---|---|
| | | 100 mM | 284 | 2.88 | 3.15 |
| | | | 287 | 3.89 | 4.16 |
| | | | 292 | 4.94 | 5.09 |
| Succinate-buffer | 3.99 5.20 | 50 mM | 286 | 2.81 | 3.42 |
| | | | 294 | 3.82 | 4.11 |
| | | | 289 | 4.89 | 5.06 |
| | | 100 mM | 287 | 2.82 | 3.31 |
| | | | 285 | 3.87 | 4.11 |
| | | | 291 | 4.95 | 5.09 |
| | | 150 mM | 290 | 2.81 | 3.24 |
| | | | 288 | 3.90 | 4.14 |
| | | | 309 | 4.97 | 5.12 |
| 3,3-dimethyl glutarate-buffer | 3.70 6.34 | 50 mM | 297 | 2.80 | 3.29 |
| | | | 289 | 3.84 | 4.16 |
| | | | 290 | 4.88 | 5.14 |
| | | 100 mM | 298 | 2.82 | 3.21 |
| | | | 293 | 3.87 | 4.14 |
| | | | 296 | 4.92 | 5.12 |
| | | 150 mM | 301 | 2.82 | 3.19 |
| | | | 297 | 3.89 | 4.14 |
| | | | 295 | 4.96 | 5.13 |

Example 4

The influences of pH and the buffer on the anticoagulant activity of heparin were tested.

A heparin-saline solution (10 units/mL) having an osmotic pressure ratio of 1.0 and being adjusted to pH 2 to 7 with 100 mM phosphate was stored at room temperature for 4 weeks to measure a titer of heparin. As a result, at pH 2.0 or less, the titer of heparin was decreased with time, while at pH 2.5 or more, the titer was slightly decreased and efficacy was sufficiently exhibited (Table 4). These results indicate that the anticoagulant action of heparin is not influenced by weakly acidifying the catheter lock solution and adding the buffer, and the efficacy of preventing thrombi in an intravascular indwelling catheter is maintained.

TABLE 4

Change in heparin activity (%) at various pH
(pH 7, 100% titer at start of storage)

| | Number of storage days | | | |
|---|---|---|---|---|
| | 1 | 6 | 14 | 28 |
| pH 7.0 | 100 | 100 | 100 | 100 |
| pH 6.5 | 100 | 98 | 100 | 99 |
| pH 6.0 | 99 | 95 | 99 | 98 |
| pH 5.5 | 101 | 99 | 102 | 100 |
| pH 5.0 | 100 | 98 | 94 | 93 |
| pH 4.5 | 97 | 100 | 91 | 93 |
| pH 4.0 | 82 | 91 | 99 | 92 |
| pH 3.5 | 87 | 90 | 96 | 87 |
| pH 3.0 | 80 | 91 | 85 | 85 |
| pH 2.5 | 92 | 92 | 81 | 72 |
| pH 2.0 | 83 | 83 | 60 | 42 |

In the comparative examples and the examples, pH was measured using, as a pH meter, TOA AUTO TITRATION (manufactured by Toa DKK Co., Ltd.) and pH METER D-21 (manufactured by Horiba, Ltd.). The osmotic pressure was measured using, as an osmometer, Osmostat OM-6040 (manufactured by Arkray Inc.). The titer of heparin was determined as the intensity of the anticoagulant action using Test Team Heparin S (Daiichi-Kagaku Yakuhin).

What is claimed is:

1. A bacteriostatic-heparin-containing catheter lock solution to be injected into an intravascular indwelling catheter, the solution comprising:
   a buffering agent selected from citrate, acetate, phthalate, succinate, and 3, 3-dimethyl-glutarate, and
   heparin or a salt thereof,
   wherein the buffering agent contains an organic or inorganic acid having an acid dissociation constant (pKa) of 3.0 to 6.5 at a concentration of 10 to 250 mM in the catheter lock solution, and
   the catheter lock solution has a pH of 3.0 to 4.97 and an osmotic pressure ratio of 0.5 to 3.0, wherein a preservative, an antimicrobial agent, or an antibiotic is not added to the catheter lock solution.

2. The catheter lock solution according to claim 1, the content of the heparin or the salt thereof includes an excess added in an amount corresponding to the activity lost under the pH.

3. The catheter lock solution according to claim 1 wherein the catheter lock solution is sterile.

* * * * *

UNITED STATES PATENT AND TRADEMARK OFFICE
CERTIFICATE OF CORRECTION

PATENT NO.        : 8,703,739 B2                                                                 Page 1 of 1
APPLICATION NO.   : 13/133123
DATED             : April 22, 2014
INVENTOR(S)       : Kimura et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 219 days.

Signed and Sealed this

Twenty-ninth Day of September, 2015

Michelle K. Lee
*Director of the United States Patent and Trademark Office*